US006379621B1

(12) United States Patent
Schwab

(10) Patent No.: US 6,379,621 B1
(45) Date of Patent: Apr. 30, 2002

(54) APPARATUS FOR ANALYZING WATER AND WASTEWATER

(75) Inventor: Ulrich Schwab, Graefelfing (DE)

(73) Assignee: WTW Wissenschaftlich-Technische Werkstaetten GmbH (DE)

( * ) Notice: Subject to any disclaimer, the term of this patent is extended or adjusted under 35 U.S.C. 154(b) by 0 days.

(21) Appl. No.: 09/401,237

(22) Filed: Sep. 23, 1999

(30) Foreign Application Priority Data

Sep. 23, 1998 (DE) .......................... 198 43 750
Oct. 11, 1998 (DE) ..................... 298 20 171 U

(51) Int. Cl.[7] ............... G01N 1/10; B01D 65/02
(52) U.S. Cl. ............ 422/68.1; 210/85; 210/321.69; 422/61; 422/101; 73/863.24
(58) Field of Search .................. 210/85, 93, 96.1, 210/321.69, 407–411, 636; 73/863.23, 863.24, 461.59, 64.56; 422/101, 68.1, 55, 58, 81, 82; 204/409–415; 436/52, 53

(56) References Cited

U.S. PATENT DOCUMENTS

| 4,404,284 A | | 9/1983 | Heider et al. |
| 4,763,537 A | | 8/1988 | Scott et al. |
| 4,921,610 A | * | 5/1990 | Ford et al. .................. 210/636 |
| 5,160,604 A | * | 11/1992 | Nakamura et al. ...... 210/321.69 |
| 5,162,077 A | | 11/1992 | Bryan et al. |
| 5,304,487 A | * | 4/1994 | Wilding et al. ................ 422/55 |
| 5,672,319 A | | 9/1997 | Eisum |
| 5,695,719 A | * | 12/1997 | Lynggaard et al. ........... 422/81 |
| 5,769,539 A | * | 6/1998 | Tsang et al. ................. 210/636 |
| 5,919,356 A | * | 7/1999 | Hood .......................... 210/85 |

FOREIGN PATENT DOCUMENTS

| DE | 41 14 959 A1 | 11/1992 |
| DE | 297 01 652 U1 | 5/1997 |
| DE | 198 19 857 A1 | 11/1998 |

* cited by examiner

*Primary Examiner*—Joseph W. Drodge
(74) *Attorney, Agent, or Firm*—Cantor Colburn LLP

(57) ABSTRACT

The invention relates to an apparatus for analyzing water and wastewater, including a housing which is immersible in the water or wastewater to be analyzed, an analyzer for determining at least one water or wastewater parameter, a membrane separating a sample space from a filtrate space, and a conduit connecting the filtrate space to said analyzer. Also described are embodiments containing device to clean or eliminate soilage from the membrane. The analyzer, membrane and conduit are located in the housing.

18 Claims, 1 Drawing Sheet

APPARATUS FOR ANALYZING WATER AND WASTEWATER

BACKGROUND OF THE INVENTION

Field of the Invention

The present invention relates to an apparatus for analyzing water and wastewater, the apparatus including a sampler. The wastewater analyzing apparatus comprises furthermore an analyzer for determining at least one water or wastewater parameter.

SUMMARY OF THE INVENTION

The invention is based on the object of providing an apparatus for analyzing water and wastewater which furnishes exact values, is insensitive to soilage and is suitable for field-analysis.

This object is achieved by an apparatus for analyzing water and wastewater as it reads from claim 1. The subject matter of the invention furthermore relates to a method for cleaning a membrane filter of a sampler in an apparatus for analyzing water and wastewater permitting safe operation both in water and clarifying tanks and requiring no separate supply of fresh water. Advantageous aspects of the invention read from the dependent claims.

In accordance with the invention for obtaining a sample the water or wastewater to be analyzed is directed through a membrane filter before then being supplied to the analyzer.

To maintain the membrane clean the complete sampler in the clarifying tank may be arranged, for example, in a region of high turbulence or strong gas supply.

Cleaning the membrane is furthermore assisted by the apparatus for analyzing water and wastewater including a separate gas feed for flushing the filter medium with gas. In this case the sampler may also be arranged in a region of a water or clarifying tank exposed to less turbulence or gas flow, the gas feeder then being preferably provided below the membrane.

The apparatus for analyzing water and wastewater may comprise e.g. a separate sample space supplied via a feed conduit from a water or clarifying tank. The membrane may also be arranged directly in a water or clarifying tank, however, so that the latter forms the sample space.

In one extremely advantageous aspect of the invention a backwash means is provided which charges the membrane from the filtrate space with fresh water or gas, as a result of which soilage of the membrane is forced into the sample space. A stand-alone apparatus independent of a fresh water and gas supply is achieved when during normal activity the filtrate from the filtrate space is stored in a permeate space and the backwash means making use of the filtered water from the permeate space for backwashing the membrane. In this case an effective cleaning of the membrane is possible without fresh water or gas. In the normal filter/analysis mode the filtrate may be continually pumped or piped into the permeate space, the effluent from the permeate space forming the overflow which is returned to the permeate space or tank. In this case the permeate space receives a continual supply of fresh permeate so that the formation of organic matter in the permeate space is eliminated. Preferably the feed and discharge to/from the permeate space are configured so that a linear flow is maintained therein in normal operation. The backwasher may be connected in addition to a cleaning agent supply, for example, to a cleaning agent tank by means of which a cleaning solution may be supplied to the filtrate space. Preferably the backwasher is formed by a pump capable of creating a suitable overflow in the filtrate space to flush out soilage, particularly of an organic nature, from the membrane in the direction of the sample space.

In another aspect of the invention, highly non-susceptible to soilage, an ultrasonic generator is arranged in the region of the membrane, preferably in the filtrate space which produces a corresponding vibration in the water in the region of the membrane and thus maintains the membrane free from clogging-up. This ultrasonic generator may be, for example, a piezo element. The ultrasonic generator is preferably controlled by the analyzer controller.

The backwasher, ultrasonic generator as well as the separate gas feeder may, of course, also be combined to eliminate soilage of the membrane more effectively in the clarifying tank soiled by organic matter.

In one highly compact and user-friendly aspect of the invention the analyzer and the sampler are configured integrated with the membrane filter in a single housing which may be immersed in a water or clarifying tank. In this case the complete water and wastewater analyzer apparatus is field-located, resulting in neither a separate location on the edge of the tank or in a building of the clarifying plant for the analyzer nor a separate sampler needing to be made available. Due to the fact that the complete sampler including sample space, filtrate space, analyzer and, where necessary, a gas feeder, an ultrasonic generator and a backwasher are all configured integrated, all that is needed is an soilage-resistant immersible housing which may be immersed in a water or clarifying tank without disturbing operation. From thus unit a cable may be led out for directly retrieving a signal for the desired water or wastewater parameter, for example, nitrate or phosphate value, nitrite or ammonia value.

It is, of course, also possible to equip the integrated arrangement with a transceiver system via which the measurement results may be wireless transmitted to a receiver in a building of the clarifying plant, for example, for central process control. The integrated device may thus receive also control parameters from an external controller. In such a wireless transmission system it would also be possible to check the operating status of the water and wastewater analyzer such as, for example, battery status, chemicals and cleaning agent status and the operating values of pumps to obtain an indication as to the pressure drop across the membrane filter.

However, the analyzer does not need to already furnish the final values, but merely values which may be interpreted by an analyzer for determining the measurement parameters. Preferably, however, the analyzer is likewise arranged in the integrated unit.

In the integrated immersible arrangement the sample space is preferably formed by a sieve or a perforated outer wall of the housing, it being in this way that ingress of coarse particles of dirt into the sample space is eliminated. In the sample space the membrane filter is then provided which is advantageously flushed by the gas feeder, the gas feed port of which is arranged in the lower portion of the sample space. The resulting turbulences clean the membrane surface. As an alternative it is, of course, just as possible to also allow the membrane filter to come into direct contact with the surrounding medium of the water or clarifying tank, as a result of which the membrane filter forms the equivalent of an outer wall of the housing.

Preferably the immersion probe is held by a positioning rod in the water or clarifying tank. Preferably the positioning rod protrudes from the water and may, for example, feature surface-mounted solar-cells for operating the electric components of the analyzer. Wiring, or conduits for feeding cleaning agents and reagents, may also be configured in the positioning rod. When use is made of solar-cells a rechargeable battery is preferably provided in the immersion probe which is charged via the solar-cells and furnishes the current needed to power pumps, electric valves or an ultrasonic unit.

BRIEF DESCRIPTION OF THE DRAWINGS

The invention will now be described by way of an example with respect to the schematic figure in which.

DETAILED DESCRIPTION OF THE INVENTION

Figure 1:
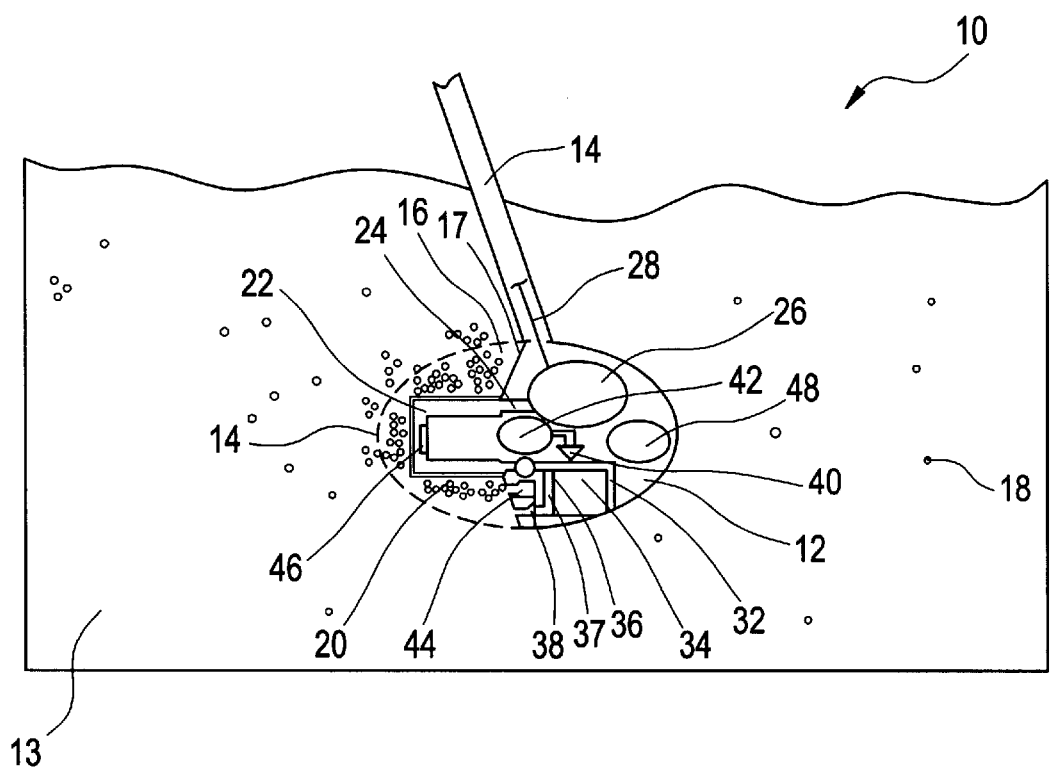
FIG. 1 is an illustration of an integrated apparatus for analyzing water and wastewater in the form of an immersion probe.

As shown in FIG. 1, the apparatus for analyzing water and wastewater 10 is configured as an immersion probe for immersion in a water or clarifying tank 13. The immersion probe 10 has a substantially rotationally-symmetrical egg-shaped housing 12 which is held below the water surface by a positioning rod 14. The rear side of the housing 12 is formed by a permeable wall 14 separating a sample space 16 from the clarifying tank 13 so that soilage 18 cannot gain access to the sample space 16. Arranged coaxially to the axis of rotation of the housing 12 in the sample space 16 is a beaker-shaped cylindrical membrane filter 20. This membrane filter 20 may be made of either a corresponding rigid material or comprise a beaker-shaped support surrounded by a thin membrane. Due to the membrane filter 20 the sample space 16 is separated from the filtrate space 22. A partition 17 separates the sample space 16 from the remaining components of the apparatus for analyzing water and wastewater 10. The filtrate space 22 is connected to the analyzer 26 via a feeder 24, the analyzer in turn being connectable by an electric connecting cable 28 to a data logger and/or power supply. The electrical data transfer and supply line 28 is run out of the water or clarifying tank 12 along the inside of the positioning rod 14. The filtrate space 22 is furthermore connected via a pump 30 and a backwash conduit 32 to a permeate space 34 which is in turn connected to the sample space via an overflow 36, a return port 37 and a first solenoid valve 38. In the normal filtration/analysis mode filtrate is continually pumped by the pump 30 via the backwash conduit 32 into the permeate space 34. Older permeate is returned via the overflow 36, return port 37 and the first solenoid valve 38 back into the sample space. As an alternative the return port could also port directly from the outer side of the housing into the clarifying tank 12. Porting into the backwash conduit 32 via a second solenoid valve 40 is the output of a cleaning agent tank 42. Via the second solenoid valve 40 the cleaning agent feed from the cleaning agent tank 42 may be opened for cleaning the filtrate space 22 and/or the permeate space 34.

As the membrane filter 20 slowly becomes sedimented in the case of normal analysis the motor 30 may be reversed and the first solenoid valve 38 closed. In this case clean filtrate is pumped from the permeate space 34 into the filtrate space 22, as a result of which the membrane filter 22 is backwashed pressurized. In this arrangement a cleaning agent may also be supplied from the cleaning agent tank 42 by suitable signaling the second solenoid valve 40 to thus permit very good cleaning of the membrane filter.

Cleaning the membrane 22 may also be achieved as an alternative or additionally by a gas feeder 42 porting into the sample space 16 below the membrane filter 20 and injecting gas bubbles or gas into the sample space so that the membrane filter is cleaned mechanically by the gas bubbles and the resulting turbulences.

For additionally or alternatively cleaning the membrane 20 an ultrasonic generator 46 is provided which in the present case is arranged in the filtrate space 22. Due to the ultrasonic vibrations the membrane filter is caused to vibrate resulting in soilage clogging the pores being quickly and effective released. The cited cleaning devices may be operated alternatively or also in combination, as a result of which effective analysis may be implement ed eve n in clarifying tanks having heavy soilage.

Provided furthermore in the housing 12 is a tank 48 for reagents or chemicals as needed for operating the analyzer 26.

The invention also specifies a method for cleaning a membrane filter (20) of a sampler in an apparatus for analyzing water and wastewater including an analyzer (26) for determining at least one water or wastewater parameter, comprising the steps:

directing a sample via a membrane (20) from a sample space (16) into a filtrate space (22) and supplying the sample to the analyzer (26), directing the filtrate from the filtrate space (22) into a permeate space (34), and backwashing the membrane (20) from the filtrate space by means of a backwasher (30–38) during backwashing, the water needed for backwashing being taken from the permeate space (34).

Preferably, in this case, permeate is continually supplied from the permeate space (34) to the filtrate space (22), and excess permeate supplied to the permeate space (34) returned as overflow into the sample space (16).

What is claimed is:

1. An apparatus for analyzing water and wastewater, comprising:

a housing which is immersible in the water or wastewater to be analyzed;

an analyzer for determining at least one water or wastewater parameter;

a membrane separating a sample space from a filtrate space; and a conduit connecting said filtrate space to said analyzer and means to clean or eliminate soilage of the membrane;

wherein said analyzer, said membrane, and said conduit are located in said housing.

2. The apparatus as set forth in claim 1 wherein said means to clean or eliminate soilage comprised a permeate space and connected to said filtrate space, and a backwasher for backwashing said membrane from said filtrate space is provided.

3. The apparatus as set forth in claim 2 wherein said backwasher is connected to said permeate space to obtain water needed for backwashing from said permeate space.

4. The apparatus as set forth in claim 3 wherein said permeate space comprises in its lower portion a feed conduit from said filtrate space and in its upper portion a return port to said sample space, or vice-versa.

5. The apparatus as set forth in claim 4 wherein said return port is connected at one end into an overflow port of said permeate space.

6. The apparatus as set forth in claim 2 wherein said backwasher or permeate space is connectable to a cleaning agent feed.

7. The apparatus as set forth in claim 6 wherein said backwasher comprises a pump and controllable electric valves for pumping water from said cleaning agent feed into said filtrate space.

8. The apparatus as set forth in claim 2 wherein said backwasher comprises a pump and controllable electric valves for pumping water from said permeate space into said filtrate space.

9. The apparatus as set forth in claim 1 wherein said means to clean or eliminate soilage comprises a gas feeder provided for flushing said membrane.

10. The apparatus as set forth in claim 9 wherein said gas feeder is arranged in said sample space below said membrane.

11. The apparatus as set forth in claim 1 wherein said means to clean or eliminate soilage comprises an ultrasonic generator provided in the region of said membrane.

12. The apparatus as set forth in claim 11 wherein said ultrasonic generator is arranged in said filtrate space.

13. The apparatus as set forth in claim 12 wherein said ultrasonic generator comprises a piezo element and is controllable by a controller of said analyzer.

14. The apparatus as set forth in claim 11 wherein said ultrasonic generator comprises a piezo element and is controllable by a controller of said analyzer.

15. The apparatus as set forth in claim 1 wherein said housing comprises a tank for reference chemicals and/or a permeate space for accommodating said filtrate.

16. The apparatus as set forth in claim 15 wherein said permeate space is defined from a clarifying tank or water tank by a strainer, grille or a perforated wall arranged at said housing.

17. The apparatus as set forth in claim 1 wherein said housing and said sample space are configured substantially rotationally-symmetrical.

18. The apparatus as set forth in claim 17 wherein said filtrate space is separated from said sample space by a cylindrical membrane running coaxial to said housing.

* * * * *